United States Patent [19]
Sayano et al.

[11] Patent Number: 5,041,133
[45] Date of Patent: * Aug. 20, 1991

[54] INTRAOCULAR IMPLANT

[75] Inventors: Reizo Sayano, Montebello, Calif.;
Eugene P. Goldberg, Tampa, Fla.

[73] Assignee: Pharmacia AB, Uppsala, Sweden

[*] Notice: The portion of the term of this patent subsequent to Jul. 21, 2004 has been disclaimed.

[21] Appl. No.: 54,216

[22] Filed: May 26, 1987

Related U.S. Application Data

[63] Continuation-in-part of Ser. No. 885,795, Jul. 14, 1986, abandoned, which is a continuation of Ser. No. 838,084, Mar. 13, 1986, Pat. No. 4,681,585, which is a continuation of Ser. No. 598,861, Apr. 11, 1984, abandoned.

[51] Int. Cl.$^5$ ................................................ A61F 2/14
[52] U.S. Cl. ........................................................ 623/6
[58] Field of Search ........................................ 623/5, 6

[56] References Cited

U.S. PATENT DOCUMENTS 4,164,794  8/1979  Spectoa et al.
4,414,694  11/1983  Choyce
4,681,585  7/1987  Sayano et al. ........................... 623/6

FOREIGN PATENT DOCUMENTS 2081469A  2/1982  United Kingdom ................... 623/5

OTHER PUBLICATIONS

Present Status of the Anterior Chamber Lens, DuPont Guery, III, M. D., Oct. 5, 1959.

*Primary Examiner*—David J. Sabella
*Attorney, Agent, or Firm*—Poms, Smith, Lande & Rose

[57] ABSTRACT

An intraocular implant having an optic lens and haptic for fixation of said lens in the posterior or anterior chamber of the eye, said implant having thermal stability sufficient to render said implant autoclave sterilizable, said implant being chemically stable when sterilized with high energy radiation, said optical lens consisting essentially of a solid thermoplastic polymer which is substantially transparent to visible light, is biocompatible, has a glass transition temperature of at least 120° C. and is thermally stable at a temperature of at least 120° C., and has a notched Izod impact strength at about one-eighth inch thickness of about at least one foot pound per inch, said thermoplastic polymer having repeating units of aromatic groups linked together by one or more of the following linkages: ether, ester, sulphone, carbonyl and imide.

10 Claims, 2 Drawing Sheets

Fig. 1.
Fig. 2.
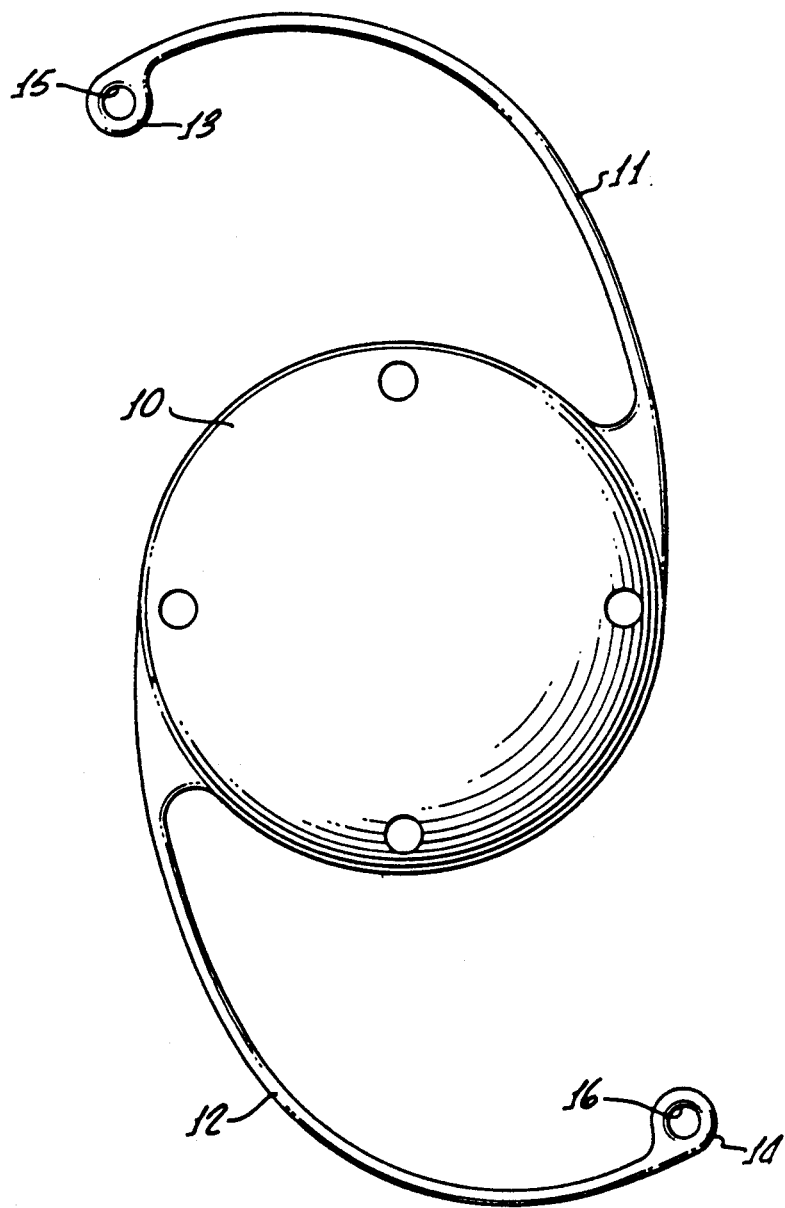
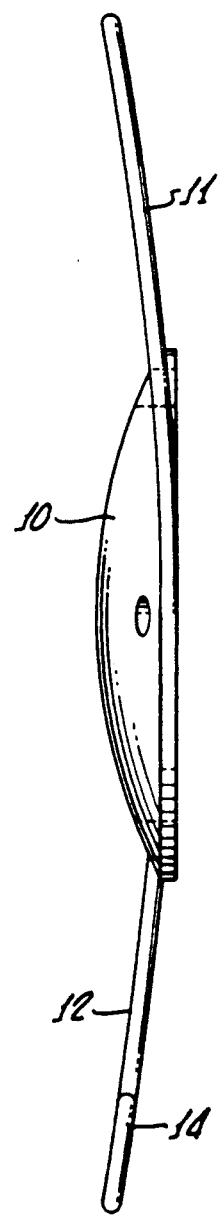

INTRAOCULAR IMPLANT

This is a continuation-in-part of co-pending application Ser. No. 885,795 filed on July 14, 1986, now abandoned, which is a continuation of co-pending application Ser. No. 839,084 filed on Mar. 13, 1986, now U.S. Pat. No. 4,681,585, which is a continuation of application Ser. No. 598,861 filed on Apr. 11, 1984, now abandoned.

BACKGROUND OF THE INVENTION

This invention relates to an improved intraocular implant which may be permanently placed within the human eye for the correction of conditions such as aphakia, myopia and corneal, retinal and other ocular impairment and re-establishment of binocularity in aphakia.

Ocular implants such as corneal lamellar inlays and intraocular lenses can be used to correct certain degenerative ophthalmic conditions and to replace the natural lens of the eye. Heretofore such ocular implants.

Intraocular lenses are exemplary of such implants and have a lens and a haptic for fixation of the lens, by a surgeon, in the anterior or posterior chamber of the human eye. The haptic may be of a variety of shapes depending, to some extent, on whether the lens is to be implanted in the anterior or posterior chamber of the eye. For example, in an article entitled "The Iridocapsular (Two-loop) Lens and Iris-Clip (Four-loop) Lens in Pseudophakia", September–October, 1973, edition of Transactions of the American Academy of Ophthalmology and Otolaryngology, there is described a surgical procedure for implanting both two-loop and four-loop intraocular lens on the iris of a human eye. These lenses were made from PMMA.

U.S. Pat. No. 4,198,714 discloses a method for implantation of an intraocular lens, preferably made from PMMA, into the posterior chamber of the human eye within the capsular membrane thereof. It is disclosed that the lens was implanted by removing a portion of the capsular membrane so that the intraocular lens could be inserted behind the iris. A first loop attached to the lens was placed in a pocket formed by the remaining portion of the capsular membrane. The iris is then pulled around the second supporting loop so that the entire lens together with its loops is placed into the posterior chamber of the human eye. It is disclosed that the anterior side of this pocket and the posterior side of the pocket eventually scar together, thereby securing the lens within the posterior chamber. Once the posterior and anterior side of the pocket of the capsular membrane have scarred together, the intraocular lens is said to be firmly, permanently and securely fixed to the capsular membrane and the iris is free to function normally. It is also taught that the use of an integral molded member eliminates edge reflections which occur in lenses implanted in the anterior chamber and internal reflections which are caused by posts for the supporting loops in other lenses implanted in the posterior chamber.

In addition to the loop attachment means described in U.S. Pat. No. 4,198,714, intraocular lenses can have other haptics such as Hessburg or J-Loop designs as well as other diverse haptic means.

Most haptics which flex, such as the haptic loops, are made of polypropylene. Polypropylene is not as brittle and has greater mechanical strength and toughness than PMMA. Nevertheless PMMA is the present plastic of choice as the lens material because it has good optical properties and has demonstrated excellent biocompatibility in the eye. However, PMMA has several disadvantages. For example, PMMA is a relatively brittle, glassy polymer with a low glass transition temperature (Tg) of about 90° C., a low thermal stability, and relatively poor mechanical strength. In addition, PMMA also transmits a substantial portion of ultraviolet light which may be harmful to the aphakic eye. In an attempt to overcome this problem prior art workers have added UV absorbers. The mechanical and optical properties of PMMA also come to issue for ocular implants such as keratoprosthesis and other corneal implants; and implants emphasizing strength and biocompatibility such as retinal tacks and glaucoma shunts.

Because of PMMA's low Tg and low thermal stability, intraocular implants made of PMMA cannot be sterilized by autoclaving with steam because of the high temperatures employed (about 120° C.–125° C.). At such temperatures PMMA becomes soft and distorted. Moreover, PMMA lenses are not sterilized using high energy radiation, e.g. Gamma sterilization at from 2 to 5 megarads, because of uncertainties regarding PMMA degradation and resulting problems of biocompatibility. Accordingly, PMMA intraocular implants are sterilized by techniques such as ethylene-oxide or other chemical or gas sterilization methods.

The use of ethylene oxide and the like for sterilization has serious disadvantages, and the Federal Drug Administration has expressed its concern by establishing maximum gas retention levels and it is known that excessive amounts may result in serious chemical burns on skin and mucous membrane irritation. Furthermore gas sterilization, for plastic which cannot withstand steam autoclave sterilization such as PMMA, takes a longer time which is not always available, or if available, can be very costly, as is the case in surgery where both labor and facilities are very costly. Ethylene oxide and its derivatives are low boiling ethers which present an added danger and therefore require additional precautions not required with steam autoclave sterilization. Ethylene oxide and other "cold" sterilization procedures are more expensive than steam autoclave sterilization.

Accordingly it can be appreciated that sterilization procedures for implantation of ocular lenses and other ocular implants need to be very short so that a minimum amount of time is required. Chemical and gas sterilization methods are generally reserved for those incidences where steam and radiation sterilization cannot be employed.

Although PMMA has heretofore been the plastic generally used for lenses it was not generally used as the haptic. However, recently there has been emphasis on a one piece or integral intraocular implant and since PMMA was the material generally used to make the lens, PMMA has been suggested and used as the haptic in integral implants. As a haptic material PMMA is much more disadvantageous than as a lens material. PMMA haptics cannot, of course, be sterilized using steam or radiation. In addition, because of PMMA's poor mechanical strength and lack of ductility, (i.e. PMMA has a notched Izod impact strength of one-eighth inch thickness of about 0.3–0.4 ft. lbs./in.) it is possible that some haptics made of PMMA will not withstand the flexing in the eye without ultimately breaking. This would be a very serious problem. Even as a lens material, PMMA's lack of mechanical strength requires thicker lenses than if a stronger plastic were used. In addition stronger and tougher plastics would allow one skilled in the art to make more versatile lens designs. Additionally, added strength would be advantageous in such applications as orbital replacement and scleral buckles to reinforce the sclera for repairing retinal tears.

Accordingly, there is a need for an intraocular implant material which is strong, ductile, easily machined or molded into thin sections, having a specific gravity of less than 2, preferably less than 1.7, and especially preferably about 1.4 or lower, which is chemically inert and stable and capable of withstanding autoclave steam sterilization without softening or permanent distortion or high energy radiation sterilization without causing an adverse change in properties.

Furthermore, there is a need to improve the effectiveness and speed with which an intraocular implant having the desired specific gravity and mechanical properties can be sterilized.

In addition, there is also a need, under certain circumstances, for an intraocular implant to be stable and withstand the energy when a laser beam is passed therethrough. For example, after removal of cataracts and the implantation of a posterior intraocular lens, in a large number of cases the posterior capsule becomes opaque. This obscures the vision and therefore requires removal of a small portion of the capsule which is located horizontally to the intraocular lens. This removal of a portion of the posterior capsule is preferably done by passing a laser beam through the intraocular lens and burning a hole in the capsule. Thus the lens must be stable to laser energy and therefore it is preferable if the lens has greater stability and strength than is possible using PMMA.

It is therefore, an object of this invention to provide an intraocular lens and/or other ocular implants and/or haptic having superior mechanical thermal and sterilization properties to that of PMMA intraocular implants.

SUMMARY OF THE INVENTION

Our invention provides an ocular said implant having thermal stability of at least 125° C. and also having the characteristic of stability when autoclaved sterilized or sterilized with high energy radiation such as Gamma radiation at from 2-5 megarads. The implant has good mechanical strength and ductility as measured by a notched Izod impact strength. This enables those skilled in the art to make thinner and more versatile lenses which are more resistant to handling and manufacturing processes than is possible with PMMA and stronger, safer, thinner integral haptic, including monofilament loop designs.

The lens itself, in addition to the properties set out above for the ocular implant, will have good optical properties and will have finished front and rear surfaces. Addressing intraocular implants in particular, such implants have an optic lens and haptics for fixation of said lens in the posterior or anterior chamber of the eye. The haptic, of course, need not have the optical properties set out above for the lens, but must possess the required mechanical strength. Haptics made of plastics, such as polypropylene, may be used in the present invention. However, it is preferred that the haptic be made of the same material as the lens in order to have an integral or one piece intraocular implant.

We have surprisingly discovered that a certain class of solid thermoplastic polymers (homo- and copolymers), preferably linear thermoplastic polymers, possess the necessary properties required to make the lens of our invention. Preferably, the haptic is also made from such thermoplastic polymers.

If the thermoplastic polymer has repeating units of aromatic groups the thermoplastic will have the desired thermal and optical properties. The remaining desired properties of the lens are achieved by having the aromatic groups linked together by one or more of the following linkages; ether, ester, carbonyl and/or imide. It should be noted that the term ester, as used herein, includes the carbonate linkage; aromatic polycarbonates are polymers coming within the scope of our invention.

The aromatic groups useful in this invention as the repeating unit of the thermoplastic polymer, include groups having an aromatic ring (including heterocyclic compounds). The aromatic groups include, but are not limited to, phenyl, biphenyl, naphthyl, anthracyl phenathryl, and alkylidenediphenyl. All of these groups may be substituted with substituents which do not adversely effect the thermal and high energy stability or biocompatability of the thermoplastic polymer, such as aliphatic (e.g. lower alkyl). Specific examples of various aromatic groups are phenyl, isopropylidenediphenyl, biphenyl, naphthyl, etc..

Among the preferred linear aromatic polyester thermoplastic polymers is linear aromatic polycarbonate which, as is known in the art, is a thermoplastic polymer in which groups of dihydric phenols are linked through carbonate groups to form the following structure:

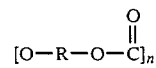

where R is aromatic, preferably isopropylidenediphenyl or phenyl and n is greater than 20, e.g. 40 to 800 or more.

Aromatic polycarbonates are tough, stiff and relatively hard plastics which maintain their properties over a wide temperature range and can have molecular weights of 200,000 or greater. For example, polycarbonate derived from bis-phenol A has a glass transition (Tg) of about 140° C. and is tough, strong and characterized by a notched Izod impact strength greater than 10 ft. lbs./in.. By "bisphenol A" as used herein it is meant para, para'-isopropylidenediphenol. Polycarbonates may be oriented and crystallized by drawing and thermal treatments. Bisphenol A polycarbonates yield transparent bodies on cooling of the melt after conventional molding or extrusion or on rapid evaporation of solvents.

The mechanical properties of aromatic polycarbonates depend on their molecular weight. For example, molecular weights above about 18,000 produce excellent tensile and impact properties. The dimensional stability of polycarbonates is very good. Polycarbonates also can be formulated and produced to have extraordinarily high impact strength. As mentioned before, polycarbonates may be oriented and crystallized by drawing and the tensile strength will be significantly increased in the direction of the stress. Index of refraction for many aromatic polycarbonates ranges from about 1.56 to about 1.66 and consequently they are optically well-suited for intraocular lenses.

Most importantly aromatic polycarbonates having an average molecular weight between 15,000 and 50,000 can be injection molded and extruded between 220° C. and 350° C. using conventional procedures and equipment. We have found that tough, durable, intraocular lenses can be produced from polycarbonates which can be formed into lightweight thin cross-sections which can be autoclaved sterilized with essentially no permanent change in lens physical and chemical properties and lens dimensions. A non-limiting example of such thermoplastic is General Electric Company's Lexan (trademark) polycarbonate. Lexan has repeating units of isopropylidenediphenyl groups connected by the carbonate ester linkage.

Another class of aromatic polyesters useful in the present invention to produce lenses and the entire implant including the haptic are linear polyarylates. These polymers are mechanically strong thermoplastics having good optical properties. Polyarylates are aromatic polyesters of phthalic acids and diphenols and have thermal stability and high notched Izod impact strength at one-eighth inch; often greater than 4 ft.-lb./in.. A preferred polyarylate is made from iso- and terephthalic acids and bisphenol A in a one to one weight ratio and has a Tg of about 170° C. Another useful polyester is that derived from Bisphenol-A, iso- and terephthalic acid and also containing carbonate linkages. This polyester has a Tg of about 160° C. and high impact strength. One example is a high temperature Lexan available from General Electric.

Another useful class of thermoplastic high impact, high temperature, transparent polymers is polyetherimides which have both ether and imide linkages. A preferred polyetherimide also contains both phenyl and isopropylidene diphenyl groups. Such a polymer has the following repeating units:

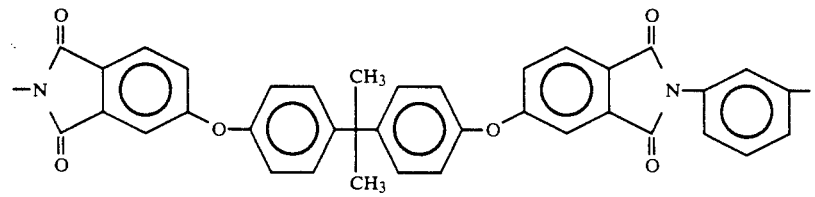

This polymer is available under the trademark Ultem from General Electric.

Another class of aromatic polymers useful in the present invention are those having carbonyl (ketone) linkages. Among the preferred carbonyl polymers are polyetherketones which are tough, strong, transparent thermoplastics having a high Tg. They are manufactured by ICI Americas Inc. and are polymers having aromatic groups which are alternately linked by an ether bridge and a carbonyl bridge.

The intraocular lenses of this invention have optically finished front and rear surfaces, edge surfaces configurations and finishes which are compatible with the eye, and a configuration which is operative for implantation without extraction of the natural lens of the eye, or both. In one embodiment of this invention the intraocular lens cross section is thin enough, that when implanted in the human eye, it will not cause significant strain to the eye.

The superior toughness and impact strength of the solid linear aromatic thermoplastic polymers over that of PMMA, enable lenses to be constructed with thinner cross sections, with more complex configurations, and with safer haptics as compared with PMMA which is a relatively brittle plastic with relatively poor impact strength, very notch-impact strength sensitive, and readily subject to stress cracking.

The material not only affords greater strength, but its optical properties and biocompatibility also make possible such implants as corneal lamellar inlays, epikeratophakia implants, and keratoprosthes. The strength and biocompatibility also allow for other ophthalmic implant uses, e.g., retinal tacks (mechanical fasteners for treatment of detached retinae), glaucoma shunts (implants designed to relieve excessive intraocular pressure by allowing aqueous outflow) and orbital replacement (implanted replacement of bone and other tissues of the orbit).

The superior mechanical properties of the aromatic thermoplastics also make practical the integral machining or molding of the intraocular lenses and haptics. Current designs with PMMA will be less safe because of the possibility of long term flexural stress cracking of PMMA.

The superior thermal and chemical stability of the aromatic thermoplastics of the present invention are also of special importance in enabling sterilization by autoclave or irradiation methods, thus making them much more useful than conventional PMMA intraocular lenses.

BRIEF DESCRIPTION OF THE DRAWINGS

FIG. 1 is an illustration in plan view of an intraocular implant for implantation in the anterior chamber of the eye.

FIG. 2 is a side view of the intraocular implant of FIG. 1.

DESCRIPTION OF THE PREFERRED EMBODIMENTS

Figure 3:
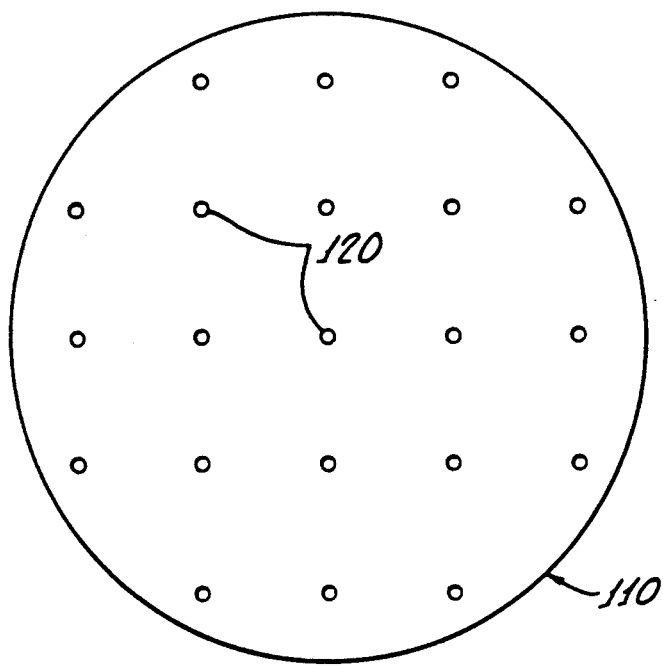
FIG. 3 is an illustration in plan view of a cornea inlay lens for implantation in the corneal stroma.

As shown in FIGS. 1 and 2 the optic lens 10 of the intraocular implant is circular and of approximately the same size as the lens of the eye. The optic lens 10 is a solid thermoplastic aromatic polymer having one or more ether, ester, carbonyl or imide linkages, and which has thermal stability in the presence of steam at a temperature of 120° C. or higher and is transparent to visible light, is biocompatible, has a glass transition temperature of at least 120° C. and has a notched Izod impact strength at one-eighth inch thickness of at least about four foot pounds per inch.

Connected to the optic lens 10 are upper haptic 11 and lower haptic 12 which are, in the exemplary embodiment, for positioning and fixing the implant in the anterior chamber of the eye. The haptics 11 and 12 are made of a solid thermoplastic polymer having the same properties as that of optic lens 10 (except for the optical properties) and, in the preferred exemplary embodiment, are made of the same thermoplastic polymer as the optic lens 10. In the embodiment of this invention shown in FIGS. 1 and 2, haptic 11 and haptic 12 are resilient so that they can be compressed when being placed in the eye but will spring out when the implant is in the correct position so that positioning element 13 of haptic 11 and positioning element 14 of haptic 12 will contact and be seated in the groove of the anterior chamber of the eye. Aperture 15 of positioning element 13 and aperture 16 of positioning element 14 are provided for grasping with forceps.

Figure 4:
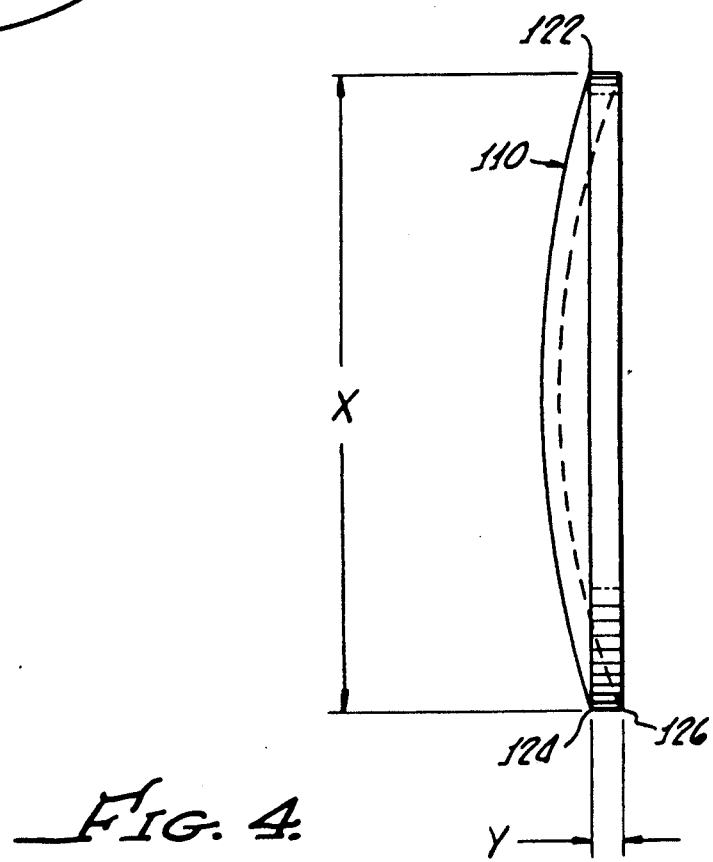
FIG. 4 is a side view of the ocular implant of FIG. 3.

Referring to FIGS. 3 and 4, an alternative exemplary embodiment of the present invention is disclosed. The implant 110 is of the type generally used in corneal lamellar inlays and is preferably placed in the corneal stroma for correction of conditions such as aphakia, myopia, and hyperopia. The implant 110 is preferably a solid thermoplastic aromatic polymer having the same characteristics as discussed with respect to the exemplary embodiment of the present invention as shown in FIGS. 1 and 2.

Referring now with particularity to FIG. 3, this embodiment of a corneal inlay lens disclosed is provided with a generally circular configuration to lens 110 and includes a number of holes or apertures 120 to allow nutrient flow from the inside of the eye to the epithelium. It is to be understood that holes 120 need not be utilized and that alternative patterns and hole sizes may be utilized as well. As best shown in FIG. 4, circumference points 122 and 124 define a lens diameter "X". Additionally, circumference point 124 and lens base point 126 define a lens thickness "Y". In the preferred exemplary embodiment, lens diameter "X" may be on the order of 5.0 mm. and lens thickness "Y" may be on the order of 0.25 mm. in thickness. However, a range of sizes and thicknesses may be employed within the scope of the present invention.

The embodiment of the present invention illustrated in FIGS. 3 and 4 is also contemplated for use in epikeratophakia implants which are placed on, in or under the corneal epithelium for certain conditions requiring optical correction. Ophthalmic uses of the material with respect to implants may also include keratoprosthesis. Keratoprosthesis is the implantation of an artificial, synthetic cornea in corneal or scleral tissue.

While not pictured, it will also be understood by those skilled in the art that other ocular implants which utilize the strength and biocompatibility afforded by the present invention are contemplated as being within the scope of the present invention.

EXPERIMENTAL RESULTS

Example 1

Intraocular implants were made having a bisphenol A polycarbonate (Lexan) optic lens and polypropylene monofilament haptics.

One eye of each of eleven New Zealand white rabbits weighing between 2.5 and 3.0 kg was implanted with the intraocular implants. Four intraocular implants were implanted without extraction of the natural lens. Seven intraocular implants were implanted with extracapsular lens extraction.

Five of the intraocular implants were autoclave sterilized and six intraocular implants were sterilized by ethylene oxide sterilization. No difference in implant behavior was noted for the autoclave sterilized intraocular lenses. The autoclave sterilized intraocular lenses performed satisfactorily.

All of the implants functioned excellently with no adverse reaction attributable to the polycarbonate during the implant period of more than one year.

What is claimed is:

1. An ocular implant, said implant having thermal stability sufficient to render said implant autoclave sterilizable, said implant having sufficient chemical stability for sterilization with high energy radiation, and consisting essentially of a thermoplastic polymer which is substantially transparent to visible light, is biocompatible, has a glass transition temperature of at least 120° C. and is thermally stable at a temperature of at least 120° C., and has a notched Izod impact strength at about one-eighth inch thickness of about at least one foot pound per inch, said thermoplastic polymer having repeating units of aromatic groups linked together by one or more linkages selected from the group consisting of ether, ester, carbonyl and imide.

2. An ocular implant according to claim 1 wherein said aromatic group is phenyl, biphenyl, naphthyl, anthracyl, phenathryl or alkylidenediphenyl.

3. The ocular implant according to claim 1 wherein said thermoplastic polymer is polycarbonate.

4. The ocular implant of claim 3 wherein the repeating aromatic groups are alkylidenediphenyl.

5. The ocular implant of claim 4 wherein said alkylidenediphenyl is para, para'-isopropylidenediphenol.

6. The ocular implant of claim 1 wherein said thermoplastic polymer is a polyarylate.

7. The ocular implant of claim 6 wherein the repeating units in said polyarylate are iso- and terephthalate and a para, para'-isopropylidenediphenol.

8. The ocular implant of claim 1 wherein said thermoplastic polymer has ether and imide linkages.

9. The ocular implant of claim 1 wherein said thermoplastic polymer has carbonyl linkages.

10. The ocular implant of claim 1 wherein said Izod impact strength is at least about four foot pounds per inch.

* * * * *